(12) United States Patent
Lysy et al.

(10) Patent No.: US 12,649,058 B2
(45) Date of Patent: Jun. 9, 2026

(54) TRANSCUTANEOUS ELECTRICAL STIMULATOR FOR TREATMENT OF FECAL INCONTINENCE

(71) Applicant: BECAPIO LTD., Misgav (IL)

(72) Inventors: Joseph Lysy, Mevaseret Zion (IL); Dan Meir Livovsky, Ofra (IL); Shahar Harari, Tel Aviv (IL); Avshalom Shenhav, Haifa (IL); Nir Goldenberg, Haifa (IL); Dotan Tromer, Moshav Hosen (IL); Arnon Hadas, Moshav Avigdor (IL); Yaakov Greenberg, Even Yehuda (IL); Ben Zion Green, Hashmonaim (IL); Rafael Marc Kaplan, Moshav Yodfat (IL); Gil Senesh, Adi (IL)

( * ) Notice: Subject to any disclaimer, the term of this patent is extended or adjusted under 35 U.S.C. 154(b) by 258 days.

(21) Appl. No.: 18/390,438

(22) Filed: Dec. 20, 2023

(65) Prior Publication Data

US 2024/0123224 A1 Apr. 18, 2024

Related U.S. Application Data

(63) Continuation-in-part of application No. PCT/IB2022/055718, filed on Jun. 20, 2022.
(Continued)

(51) Int. Cl.
*A61B 17/42* (2006.01)
*A61N 1/04* (2006.01)
(Continued)

(52) U.S. Cl.
CPC ....... *A61N 1/36007* (2013.01); *A61N 1/0456* (2013.01); *A61N 1/0476* (2013.01);
(Continued)

(58) Field of Classification Search
CPC . A61B 17/42; A61B 2090/065; A61B 5/0004; A61B 5/227; A61B 5/296;
(Continued)

(56) References Cited

U.S. PATENT DOCUMENTS

| | | |
|---|---|---|
| 5,571,118 A | 11/1996 | Boutos |
| 2015/0290450 A1 | 10/2015 | Kolb et al. |
| 2019/0099203 A1* | 4/2019 | Blurton ................. A61B 17/42 |

FOREIGN PATENT DOCUMENTS

| | | | |
|---|---|---|---|
| WO | 2020033883 A1 | 2/2020 | |
| WO | WO-2020205431 A1 * | 10/2020 | ............. A63B 23/20 |

OTHER PUBLICATIONS

PCT International Search Report for International Application No. PCT/IB2022/055718, mailed Sep. 16, 2022, 3pp.
(Continued)

*Primary Examiner* — Jon Eric C Morales
(74) *Attorney, Agent, or Firm* — The Roy Gross Law Firm, LLC; Roy Gross

(57) ABSTRACT

A system includes at least one electrode configured for transcutaneous stimulation of a pudendal nerve or surrounding perianal tissue or both. The at least one electrode is coupled to a substrate that includes a rectal portion and a buttocks support portion. The rectal portion includes a fecal blocking element. A control module is coupled to the at least one electrode, and includes a microprocessor for controlling operational parameters of the system.

17 Claims, 8 Drawing Sheets

Related U.S. Application Data

(60) Provisional application No. 63/212,784, filed on Jun. 21, 2021.

(51) Int. Cl.
*A61N 1/36* (2006.01)
*G16H 20/00* (2018.01)

(52) U.S. Cl.
CPC ....... *A61N 1/0496* (2013.01); *A61N 1/36031* (2017.08); *G16H 20/00* (2018.01)

(58) Field of Classification Search
CPC ......... A61B 5/313; A61B 5/388; A61B 5/391; A61B 5/395; A61B 5/397; A61B 5/6804; A61B 5/7225; A61B 5/7435; A63B 23/20; A61N 1/36007
See application file for complete search history.

(56) References Cited

OTHER PUBLICATIONS

PCT Written Opinion for International Application No. PCT/IB2022/055718, mailed Sep. 16, 2022, 5pp.

* cited by examiner

30

32

34

16

12

10

TRANSCUTANEOUS ELECTRICAL STIMULATOR FOR TREATMENT OF FECAL INCONTINENCE

CROSS REFERENCE TO RELATED APPLICATIONS

This application is a Continuation-in-Part of PCT Application No. PCT/I132022/055718 having International filing date of Jun. 20, 2022, which claims the benefit of priority of U.S. Provisional Patent Application No. 63/212,784, filed Jun. 21, 2021, the contents of which are all incorporated herein by reference in their entirety.

FIELD OF THE INVENTION

The present invention relates generally to a system which combines mechanical aids with a transcutaneous electrical stimulator for treatment of fecal incontinence.

BACKGROUND OF THE INVENTION

The lower gastrointestinal (GI) tract is responsible for the storage and periodic elimination of feces. Feces are stored in the descending and sigmoid colon, which serves as a fecal reservoir, and are eliminated through the rectum and anus, which serves as the fecal outlet.

Anal closure is maintained by both smooth muscle contractions promoted by the efferent sympathetic axons in the hypogastric nerve through alphal adrenergic receptors and by striated muscle contractions of the external anal sphincter promoted by efferent somatic motor axons in the pudendal nerve through nicotinic cholinergic receptors. As the descending and sigmoid colon fill with increasing volumes of feces, stretch receptors send signals through intrinsic and extrinsic GI reflex pathways to tighten the smooth and striated muscle of the external anal sphincter, as well as inhibit sacral parasympathetic defecation reflex pathways.

As feces are propelled into the descending and sigmoid colon via peristalsis, the rectum begins to stretch, which inhibits peristalsis in the descending colon and contracts the rectum and anal sphincters. As the rectum is stretched to the point where voiding (also termed defecation) should occur, the rectal stretch receptors relay this sensory information to the brain, which can suppress the rectal sensations and the sacral parasympathetic defecation reflexes, while promoting the colon storage reflexes, until defecation is appropriate. When defecation is appropriate, the sacral parasympathetic defecation reflex is activated to relax the striated external anal sphincter, contract the sigmoid colon, and propel feces into the rectum, which simultaneously relaxes and stretches as it accepts the feces. The rectal stretching activates the recto-anal inhibitory reflex that relaxes the smooth muscle of the internal anal sphincter. Thus, contraction of the sigmoid colon coordinated with relaxation of the anal sphincters produces efficient defecation.

Fecal incontinence is the involuntary loss of feces and can be caused by dysfunction of either the voiding or storage reflexes or both. Stress incontinence, which is an involuntary loss of feces upon physical exertion (e.g., sporting activities or laughing, sneezing or coughing), is considered a weakness in storage reflexes and sphincter function. Urge incontinence, which is an involuntary loss of feces associated with episodic colon contractions and/or sensations of urgency, is considered an over-activity of the voiding reflexes. Some individuals are diagnosed with mixed incontinence, which is a combination of stress and urge fecal incontinence. Fecal incontinence affects quality of life and participation in social and professional activities.

SUMMARY OF THE INVENTION

The present invention seeks to provide a transcutaneous electrical stimulator for treatment of fecal incontinence, as is described more in detail hereinbelow.

The system of the invention provides mechanical closure of the tissue surrounding the anal cavity. It causes transcutaneous electrical stimulation of the pudendal nerve and the surrounding perianal tissue (skin, fat and muscle), thereby raising the pressure of the anal canal and contracting the external anal sphincter.

BRIEF DESCRIPTION OF THE DRAWINGS

The present invention will be understood and appreciated more fully from the following detailed description taken in conjunction with the drawings in which.

DETAILED DESCRIPTION

Figure 1:
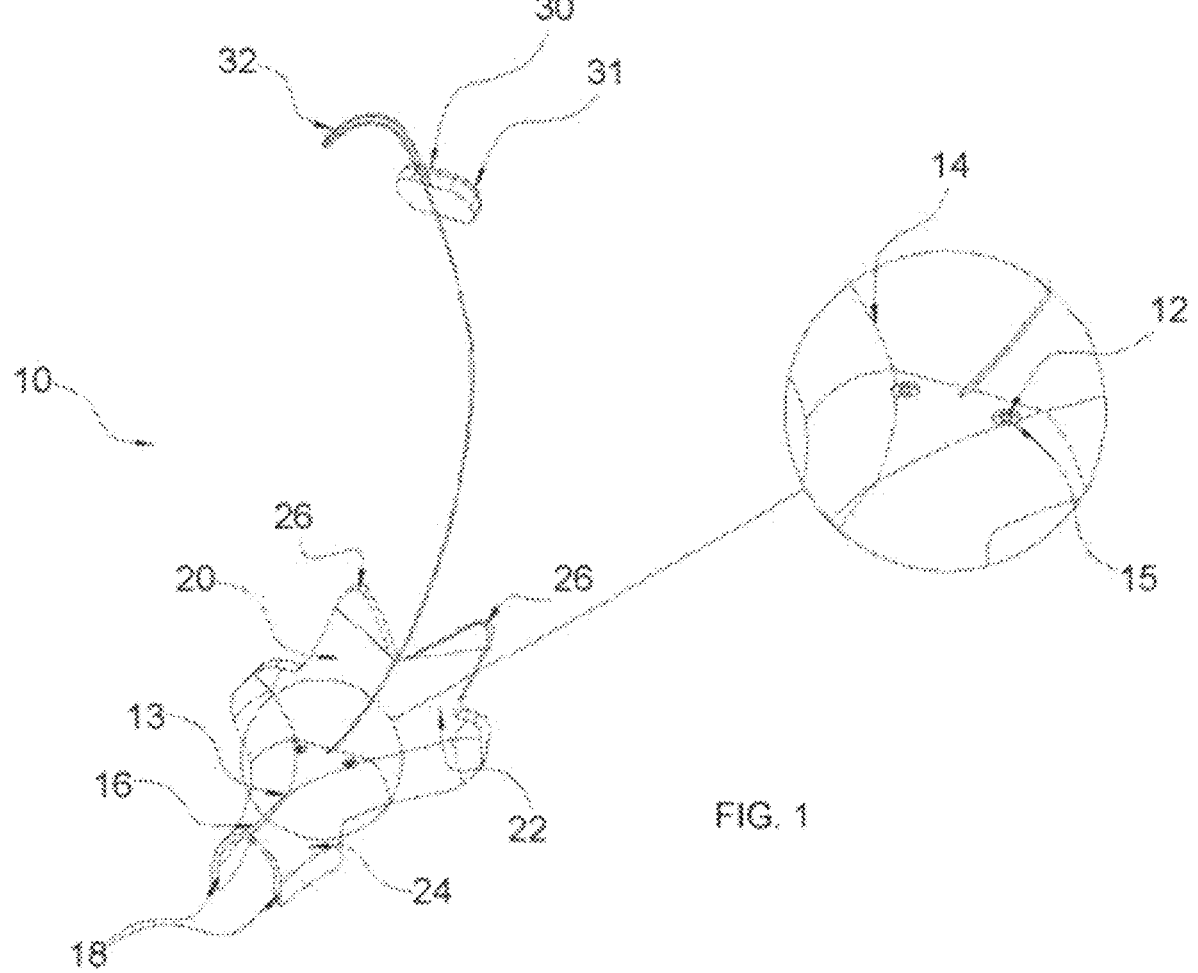
FIG. 1 is a simplified illustration of a transcutaneous electrical stimulation system for treatment of fecal incontinence, in accordance with a non-limiting embodiment of the present invention, with an external control module.

Reference will now be made in detail to non-limiting embodiments of this disclosure, embodiments of which are illustrated in the accompanying figures. The embodiments are described below by referring to the figures, wherein like reference numerals refer to like elements. When similar reference numerals are shown, corresponding description(s) are not repeated, and the interested reader is referred to the previously discussed figure(s) for a description of the like element(s). As used throughout this description, the word "proximal" means situated nearer to the skin of the body or the point of attachment of the system in the present disclosure. The words "time period" mean the length of time during which an activity occurs or a condition remains, being at least 2 seconds in length.

Described here is a system and method thereof to treat fecal incontinence. This system, and its variations, are generally sized and configured to cover the entire anal sphincter region of a user. In some embodiments, the system may include one or more features (e.g., fecal blocking element, position sensors) or may otherwise be configured to provide accurate positioning and placement of the system over the anal opening. Accurate positioning of the system may enable precise emplacement of the stimulation electrodes in the vicinity of the fecal blocking element and pudendal nerve or surrounding perianal tissue or both.

The system, and its described variations, may be placed and secured in the intergluteal cleft of a user, while folded in a manner providing sealing at all times and matching the curvatures of the anatomy. Generally, the system may be comprised of a multi-layer substrate 14 with a rectal portion 16 and a buttocks support portion 20. The rectal portion 16 may comprise a fecal blocking element with or without layers of absorption material, and the buttocks support portion 20 may comprise rigid or semi-rigid portions with flexible portions. For example, the parts on the proximal side that fit tight to the anus may be soft and flexible, whereas the buttocks supporting portions may be more rigid or semi-rigid. The rectal portion or buttocks support portion may further comprise an adhesive portion configured to prevent lateral movement of the substrate against a skin surface during use. The substrate may be coupled to at least one electrode configured for transcutaneous stimulation of a pudendal nerve or surrounding perianal tissue or both. Ultimately, transcutaneous stimulation of nerves or muscles may operate synergistically with the substrate, which provides constant mechanical closure of the tissue surrounding the anal cavity, to prevent expulsion of feces from the system.

In some embodiments, the adhesive portion may comprise two adhesive layer types, including a light skin adhesive layer for initial positioning and medium or strong skin adhesive layer for complete installment. Both adhesive layer types may be configured to enable absolute proximal interface between the substrate and skin surface during use. Moreover, the adhesive layer types may prevent substrate lateral movement against a skin surface and enable easy removal and disposal of the substrate after use.

In some embodiments, the adhesive portion may enable absolute proximal interface between the electrodes and skin surface of a user. Hence, the adhesive portion may provide increased transmission of electrical stimulation with lower resistance for a prolonged time period. Without limitation, the prolonged time period may be selected from the group consisting of at least one hour, at least two hours, at least four hours, at least six hours, at least eight hours, at least ten hours, at least twelve hours, at least sixteen hours, at least twenty hours and at least twenty-four hours.

In some embodiments, the substrate may be characterized by a shape selected from the group consisting of an elongate rectangular shape, an oval shape, a saddle shape, a G-string shape, and a garment shaped as underwear or panties.

Reference is now made to FIG. 1, which illustrates a transcutaneous electrical stimulation system 10 for treatment of fecal incontinence, in accordance with a non-limiting embodiment of the present invention.

The system 10 may include one or more electrodes 12 configured for transcutaneous stimulation of the pudendal nerve or the surrounding perianal tissue (skin, fat and muscle) (or both), thereby raising the pressure of the anal canal and contracting the external anal sphincter. Non-limiting operational parameters of the electrodes include current, pulse width, pulse frequency, pulse interval, and others.

Suitable electrodes include, without limitation, TENS (transcutaneous electrical nerve stimulation), EMS (electrical muscle stimulation), ECG (electrocardiogram), and EMG (electromyography) skin electrode pads, commercially available from many sources.

Preferably there are two or more electrodes 12, symmetrically placed about a midline 13 of an electrode substrate 14. Each electrode 12 may be mounted on the substrate 14 by any joining method, such as, but not limited to, sewing, bonding, mechanical fasteners and many more. An electrode gel 15 may be placed in the vicinity of each electrode 12. The electrodes 12 may be positioned at any place around the rectum.

The substrate 14 (also referred to as pad 14) is preferably, but not necessarily, flexible, and may be made of relatively rigid or semi-rigid materials, such as plastic or leather, or relatively flexible or compliant materials, such as cloth or polyether-polyurea copolymer, commercially known as SPANDEX or LYCRA. Such a substrate 14 allows the patient's skin to breathe and is stretchable to fit many different anatomies. For example, without limitation, the substrate may be made of a gas permeable material, such as cotton core spun LYCRA woven with polyester warp, which can allow passage of gases from the anus, and provides good air permeability and water vapor permeability. The substrate 14 may be made of a combination of rigid or semi-rigid and soft, flexible materials; for example, the parts that fit tight to the anus may be soft and flexible, whereas the buttocks supporting portions may be more rigid or semi-rigid. These features also apply to any of the other substrates (including pads, garments, etc.) described herein. The materials used for any of the substrates allow for easy removal with reduced pain or no pain at all. Also, intentional peeling of the adhesive portion during detachment and disposal of the system may enable instantaneous removal of the electrodes. For example, the adhesive may be a silicone bandage adhesive which peels off easily without ripping skin or pulling out hairs. Alternatively, the system may heat the area of the adhesive, or emit a gel and the like, to reduce the adhesiveness and allow easier, pain-free removal. In another embodiment, the system may generate electrical stimulation of the pudendal nerve and the surrounding perianal tissue (skin, fat and muscle), thereby contracting the muscles to reduce the adhesiveness and allow easier, pain-less removal. In the illustrated embodiment, the substrate 14 has a saddle shape that includes a rectal portion 16 (corresponding to the "pommel" of the saddle) from which extend side flaps 18, such as left- and right-side flaps 18. The rectal portion 16 may be curved to sit properly in the anus of the user and serve as a fecal blocking element, which stops fecal matter from exiting the anus. Moreover, the fecal blocking element may provide tactile feedback by palpation for accurate positioning and placement of the system over the anal opening. In all embodiments, the rectal portion 16 may include one or more additional layers of absorption material, such as super absorbent polymer (SAP).

The saddle shape of the substrate 14 further includes two buttocks support portions 20 (corresponding to the "cantle" of the saddle). The buttocks support portions 20 may include adhesive portions 22, such as with a removable liner, which when removed, exposes an adhesive for sticking the adhesive portions 22 to the buttocks of the user. Similarly, the rectal portion 16 may include adhesive portions 24, such as with a removable liner, which when removed, exposes an adhesive for sticking the adhesive portions 24 to the rectal area of the user.

Two types of adhesives may be used; a weaker adhesive for initial positioning and a stronger adhesive for complete installment (e.g., a two-stage glue).

The buttocks support portions 20 and the rectal portion 16 may include one or more non-adhesive areas 26, for easy removal of the pad 14.

The electrodes 12 may be electrically coupled to a control module 30, such as by means of a wired connection 32 (or wirelessly connected, such as by BLUETOOTH or other wireless connection). In the embodiment of FIG. 1, the control module 30 is external to the substrate 14. The control module 30 includes a controller (e.g., microprocessor) for controlling all the operational parameters of the system.

The system has a power source 31, e.g., rechargeable batteries (or regular batteries). The system may have an on/off switch configured to activate targeted electrical stimulation, which, for example, may be activated when the user squeezes the buttocks together, or which is activated when the EMG sensors sense an urge to defecate, or when the impedance sensors, capacitance sensors, wetness sensors, pH sensors or temperature sensors sense a leak of feces. The user has the option to turn off the system when it is necessary to defecate.

Figures 2A, 2B:
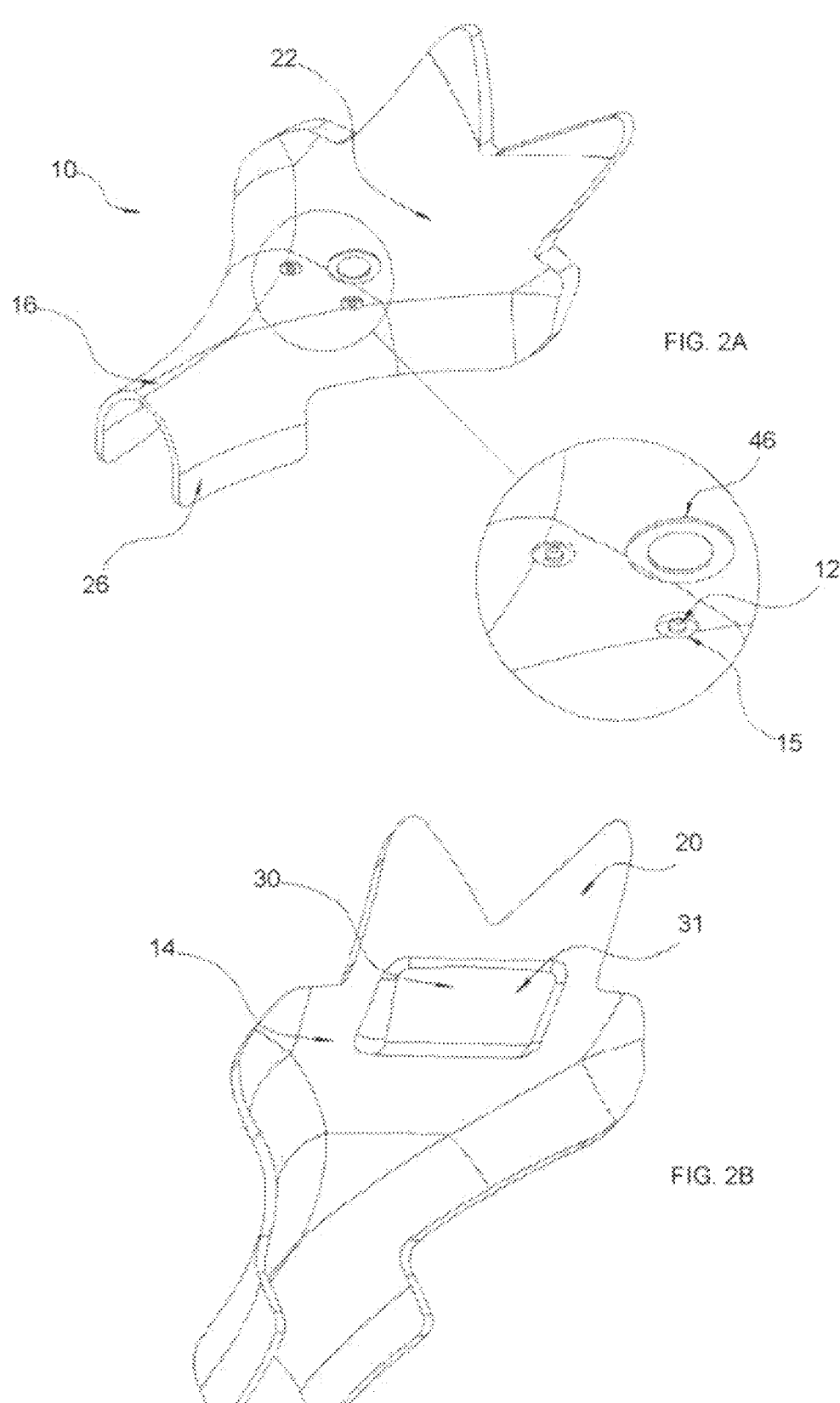
FIGS. 2a and 2B are simplified illustrations of a transcutaneous electrical stimulation system for treatment of fecal incontinence, in accordance with another non-limiting embodiment of the present invention, with an integral control module.

Reference is now made to FIGS. 2A and 2B, which illustrate another version of transcutaneous electrical stimulation system 10, in which there are one or more control modules mounted on the substrate 14, such as, but not necessarily, on the rear side of substrate 14.

Figure 3:
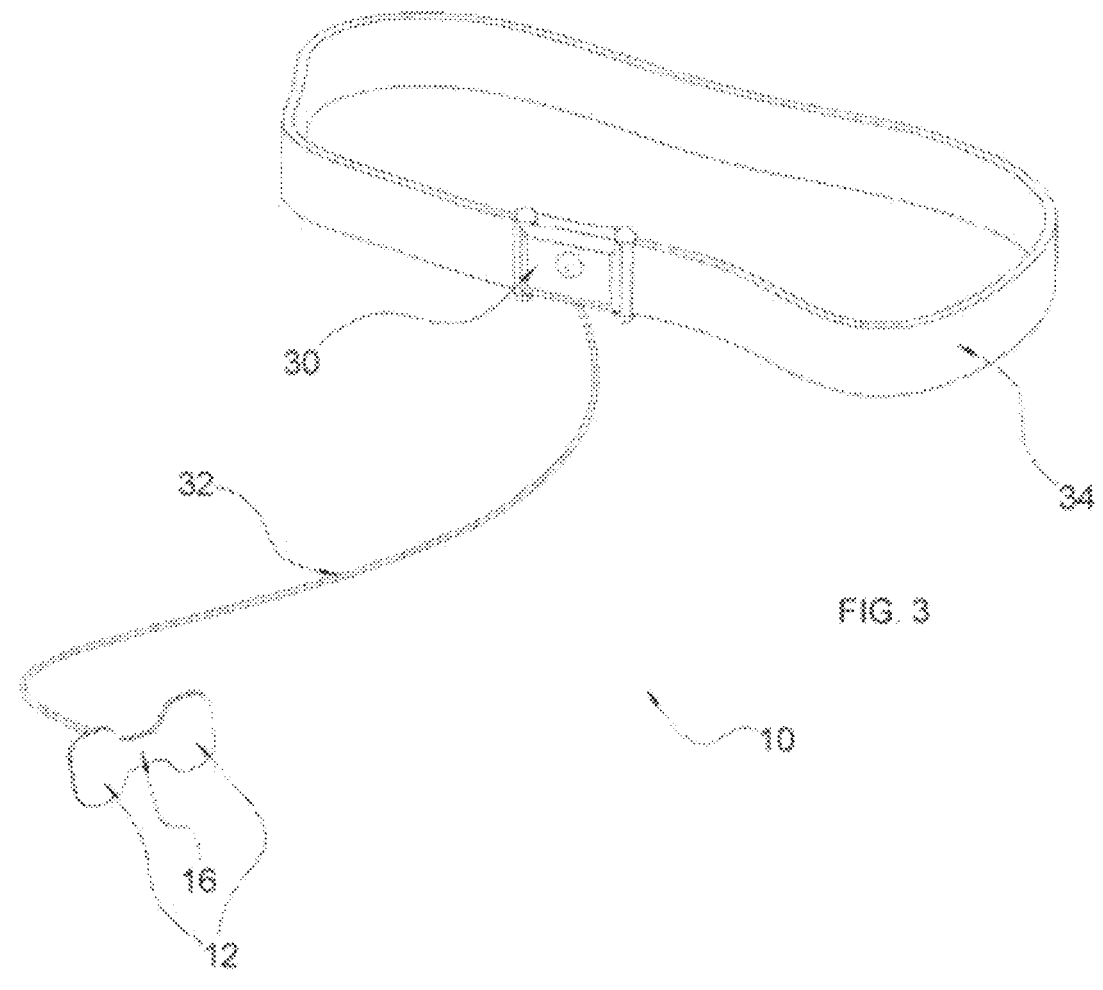
FIG. 3 is another version of the transcutaneous electrical stimulation system with an external control module mounted on a belt.

Reference is now made to FIG. 3, which illustrates one example of the external control module 30, in which it is mounted on a belt 34. In this embodiment, the substrate is not shaped as a saddle, but instead is shaped as an elongate rectangular or oval pad, or as a G-string shaped device with the electrodes 12 placed around the rectum. These shapes may alleviate the amount of stress the pad applies to the patient, and may help force the pad between both butt cheeks. They may also provide reinforcement to the adhesiveness of the patch to the buttocks. Here, too, the rectal portion 16 is configured to sit in the anus of the user and serve as a fecal blocking element, which stops fecal matter from exiting the anus.

Figure 4:
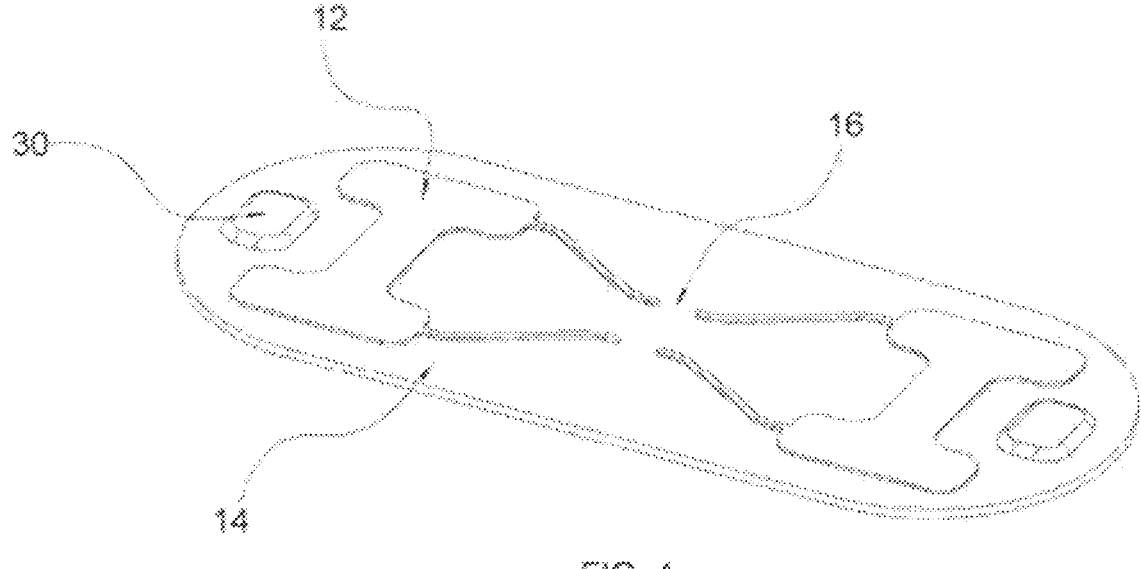
FIG. 4 is another version of the transcutaneous electrical stimulation system with an integral control module.

Reference is now made to FIG. 4, which illustrates the exemplary elongate rectangular or oval pad 14, but with the controller 30 or controllers 30 mounted on the pad 14, and not external as in FIG. 3.

Figures 5A, 5B:
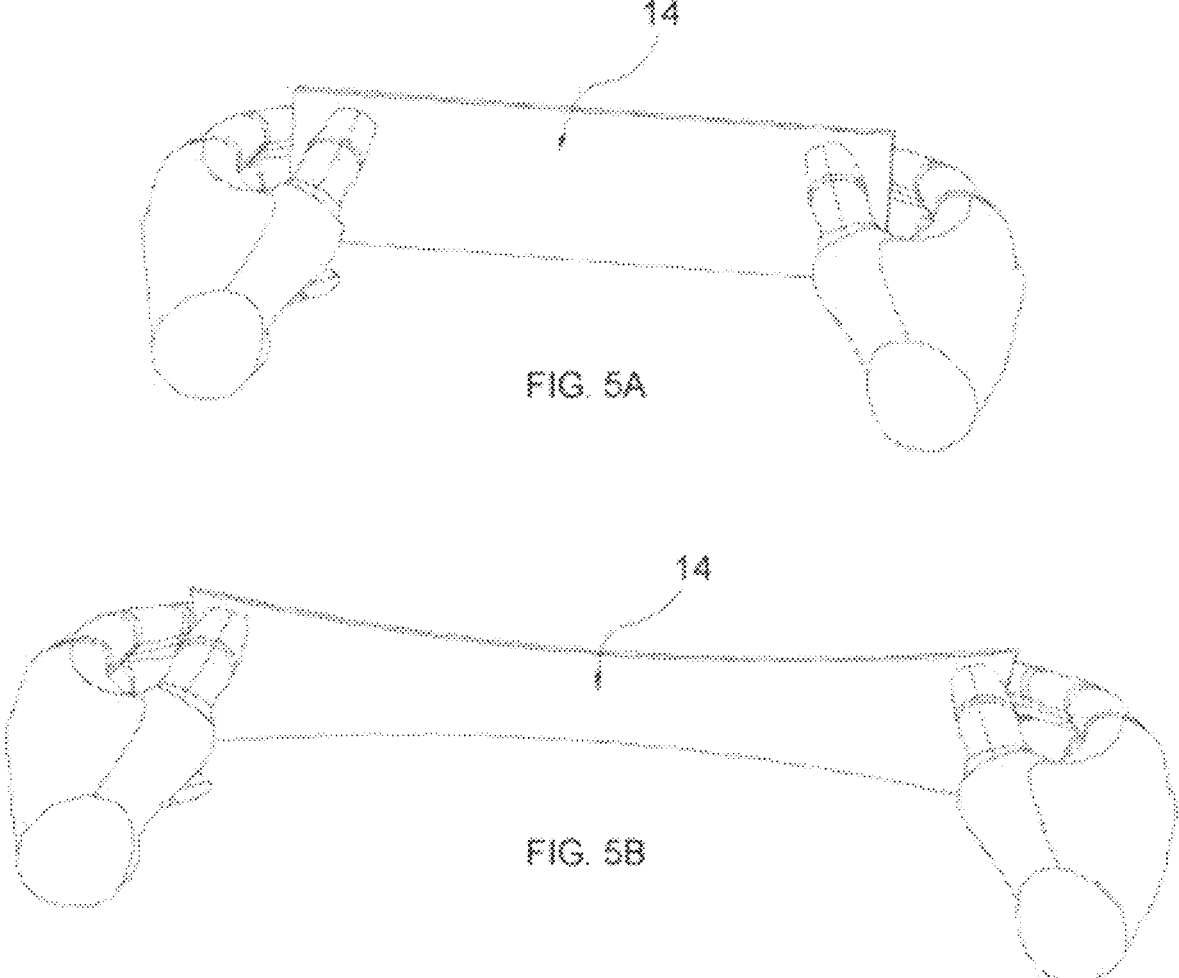
FIGS. 5A and 5B illustrate the system of FIG. 3 or 4, respectively, before and after stretching the flexible electrode substrate.

FIGS. 5A and 5B illustrate the pad 14, respectively, before and after stretching. The ability of the pad 14 to stretch enhances the ability of the pad to fit many different anatomies and to self-center properly in the anus.

Figure 6:
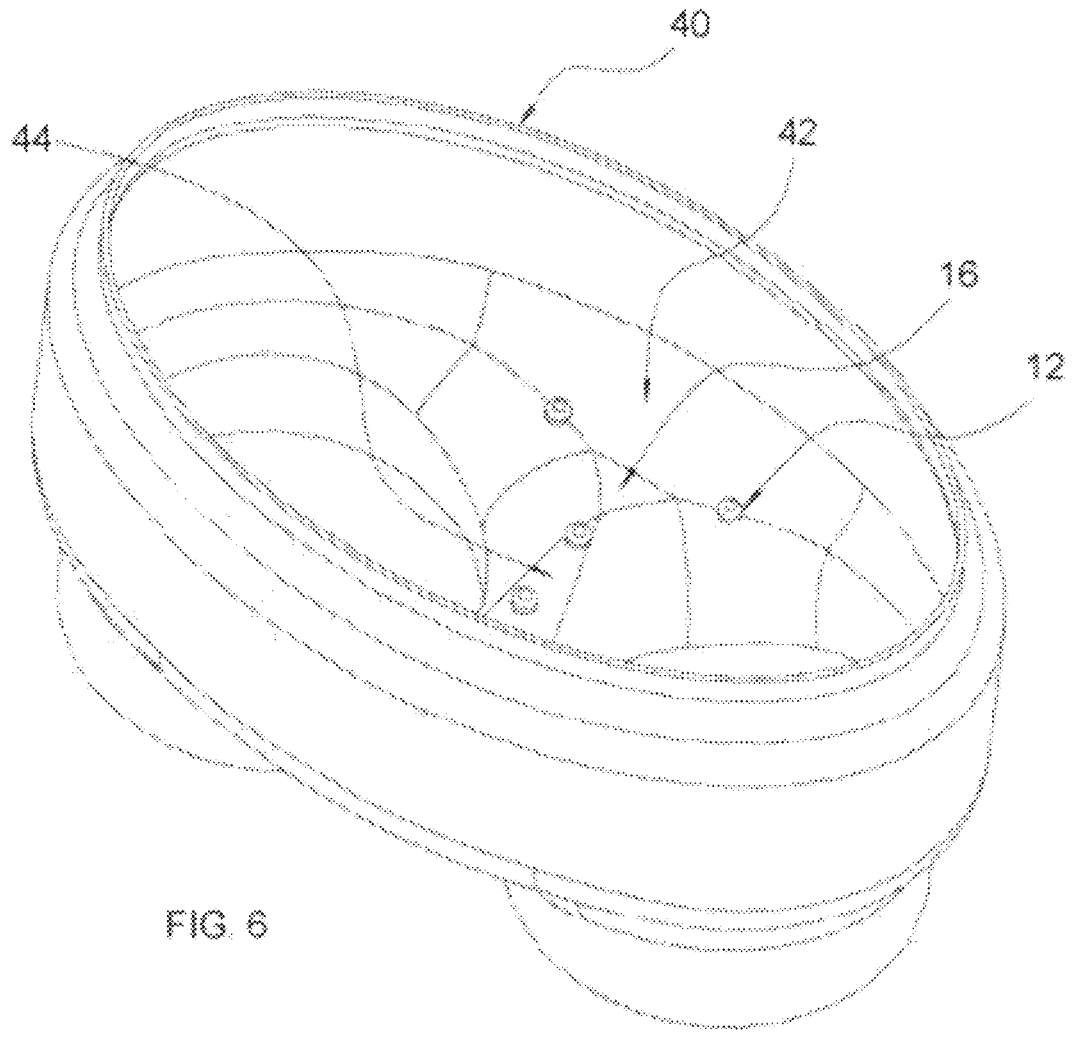
FIG. 6 is a simplified illustration of a transcutaneous electrical stimulation system for treatment of fecal incontinence, in accordance with another non-limiting embodiment of the present invention, configured as a wearable garment.

Reference is now made to FIG. 6, which illustrates yet another version of the transcutaneous electrical stimulation system, in which the substrate is configured as a wearable garment 40, such as underwear or panties. The garment 40 may include a rectum patch or pad 42, and a perineum patch or pad 44, each of which includes one or more stimulation electrodes 12. Here, too, the crotch area of the garment 40 has a rectal portion 16 which is configured to sit in the anus of the user and serve as a fecal blocking element, which stops fecal matter from exiting the anus.

Figure 7A:
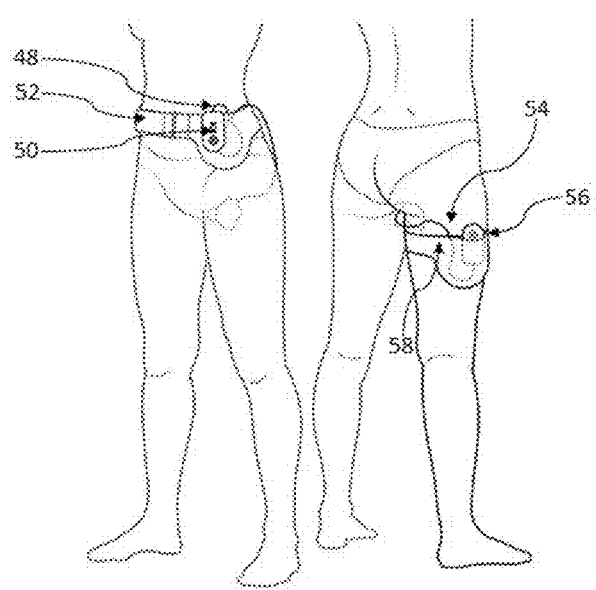
FIGS. 7A, 7B and 7C are simplified illustrations of a transcutaneous electrical stimulation system for treatment of fecal incontinence, in accordance with another non-limiting embodiment of the present invention, showing various features of an external control module.
Figure 7B:
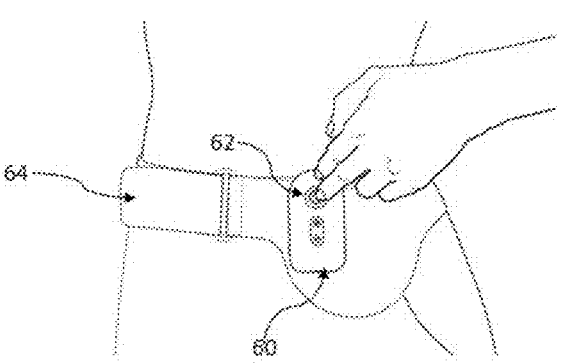
Figure 7C:
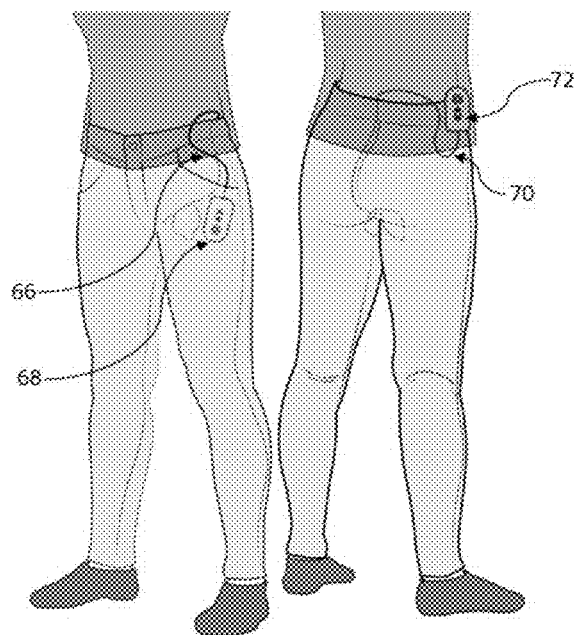

FIG. 7A is a simplified illustration of a transcutaneous electrical stimulation system with an external control module, in accordance with a non-limiting embodiment of the present invention. In the anterior view, the wire 48 which connects with the control module 50 exits the back of the user through the center of the buttocks and is attached with an integrated docking solution, e.g., an elastic or non-elastic belt 52, independent of clothing. In the posterior view, the wire 54 which connects with the control module 56 is attached with another integrated docking solution, e.g., elastic or non-elastic thigh strap 58, independent of clothing. FIG. 7B is a simplified illustration of a transcutaneous electrical stimulation system with an external control module 60 as shown in FIG. 7A, wherein the control module 60 has an on/off switch 62 configured to activate targeted electrical stimulation and is attached with an integrated docking solution, e.g., an elastic or non-elastic belt 64, independent of clothing. FIG. 7C is a simplified illustration of a transcutaneous electrical stimulation system with an external control module, in accordance with a non-limiting embodiment of the present invention. In the anterior view, the wire 66 exits the back of the user through the center of the buttocks and is attached to the control module 68 placed in the pocket of a pair of trousers worn by a user. In the posterior view, the wire 70 exits the back of the user through the center of the buttocks and is attached to the control module 72, which is attached with a clip to a pair of trousers worn by a user.

Figure 8A:
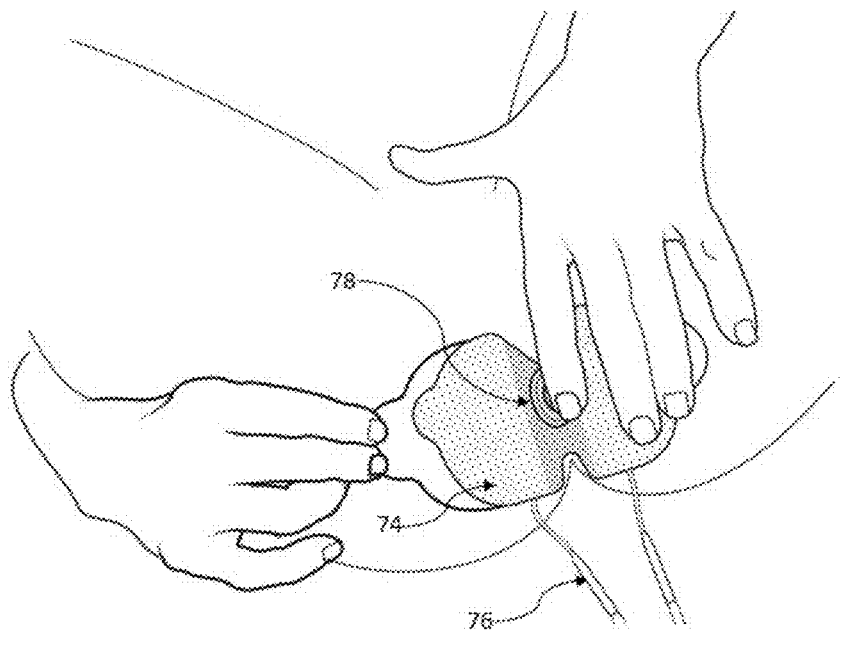
FIGS. 8A and 8B are simplified illustrations of affixing and detaching a transcutaneous electrical stimulation system by a user, respectively, according to a specific embodiment of the present invention.
Figure 8B:
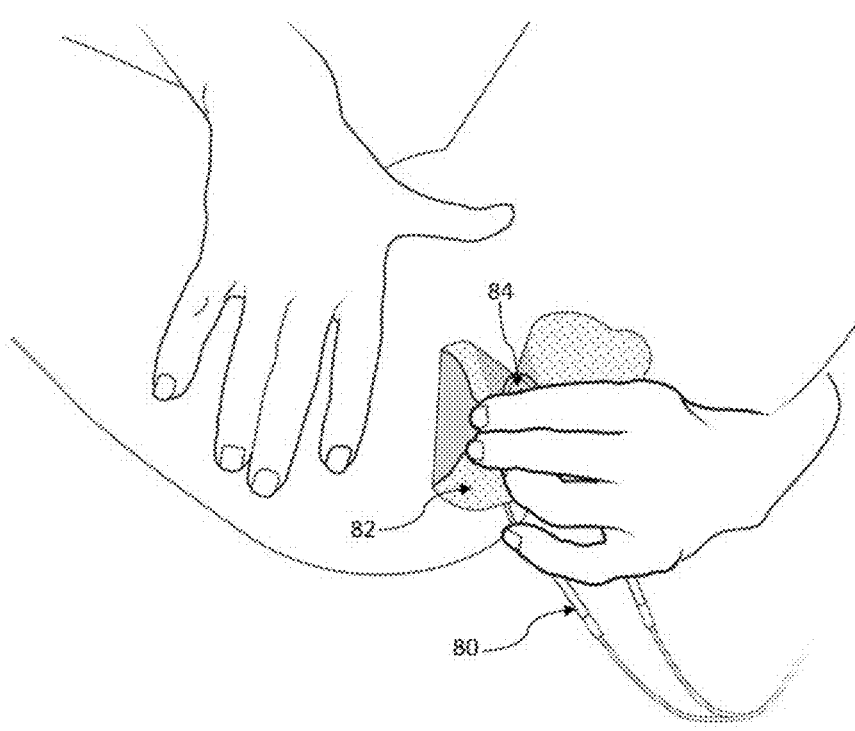

Reference is now made to FIG. 8A, which illustrates affixing a transcutaneous electrical stimulation system 74 by a user, in accordance with a non-limiting embodiment of the present invention, wherein the wire 76 attached to the electrodes exits the back of the user through the center of the buttocks and is attached to the control module. The fecal blocking element 78 may provide tactile feedback by palpation of the rectum, thus enabling accurate positioning and placement of the device by the user over the anal opening with the adhesive portion. FIG. 8B is a simplified illustration of detaching a transcutaneous electrical stimulation system by a user, in accordance with a non-limiting embodiment of the present invention, wherein the wire 80, attached to the electrodes in the substrate 82 with a fecal blocking element 84, exits the back of the user through the center of the buttocks and is attached to the control module. The peeling of the adhesive portion of the substrate during detachment and disposal of the system may enable instantaneous removal of the electrodes.

In all embodiments of the invention, the control module 30 may alternate the peripheral stimulation between the left and right in the buttocks of the anal sphincters. The system may select an appropriate stimulation pattern and modify the stimulation pattern with feedback from sensors, including monitoring and modulating the peak (sphincter pressure at the beginning of the stimulation) and the end pressure (sphincter pressure at the end of the stimulation) on the anal sphincters and nerves. The electrical stimulation may be combined with voluntary contraction of anal sphincter muscles to increase contraction forces until the fecal urge sensation is dismissed.

Without limitation, the stimulation pattern may employ continuous or intermittent stimulation (e.g., on and off every 5-45 seconds, or any other time interval). The changing stimulation frequencies may be, without limitation, between 10 and 40 Hz. Changes in pulse width may be, without limitation, 100-500 µs, and the system may take into account previously determined optimal current strength (for reaching saturation). The current range supplied to the electrodes may be, without limitation, between 0.5 and 10 mA.

In all embodiments of the invention, the control module 30 may operate in a control feedback loop with one or more sensors 46 (shown in FIG. 2) that sense biological information for use with the system. The one or more sensors may obtain measurements associated with muscle activity or neurological activity, or both, following the transcutaneous stimulation. Non-limiting examples of such sensors are now described.

Electromyography (EMG) sensors may be used to sense the electrical activity of the anal sphincter muscles, which can indicate the patient's urge for defecating and the patient's response to the stimulation provided by the electrodes.

Sensors may be used to detect when a bit of fecal matter has been excreted, such as wetness sensors, impedance sensors, capacitance sensors, temperature sensors or pH sensors.

Position sensors may be used to detect when the system is properly positioned, that is, the rectal portion 16 is properly positioned in the anus of the user to serve as the fecal blocking element, and that the electrodes 12 are properly aligned with the pudendal nerve and the surrounding perianal tissue. Furthermore, sensors may be used to provide an indication to the user that the system is on or off, and that the electrodes are connected and working (conductivity check test). In further embodiments, the transcutaneous stimulation is based on learning of an effect and an occurrence of previous stimulation on a user. The learning may be used to predict defecation and to activate electrical stimulation autonomically. The system may use a data logger with memory to store measurements deriving from the aforementioned array of sensors, patient behavior, stimulation parameters and patient reaction to these stimulation parameters, to study and improve the stimulation provided to the patient, in order to optimize the desired effect on the patient. Accordingly, measurements deriving from the aforementioned array of sensors may be reported to the patient or physician and used to predict fecal incontinence frequency and patterns. External data may also be inputted into the system, such as, but not limited to, dietary or nutritional recommendations, information regarding prescription drugs and medicines being administered to the patient (and their effect on the stimulation and fecal incontinence), physical activity, day-to-day behaviors, mental and physical stress; the external data may be taken into consideration by the controller to plan or modify treatment protocols (e.g., electrical stimulation properties) of the system per patient.

What is claimed is:

1. A system for treatment of fecal incontinence comprising:

a multi-layer substrate characterized by a shape configured to cover the entire anal sphincter region of a user; said multi-layer substrate comprises a rectal portion and a buttocks support portion; said rectal portion comprises a fecal blocking element with or without layers of absorption material; said buttocks support portion comprises rigid or semi-rigid portions with flexible portions;

wherein said rectal portion or said buttocks support portion further comprise an adhesive portion configured to prevent lateral movement of said substrate against a skin surface during use;

wherein said substrate is coupled to at least two electrodes positioned symmetrically about a midline of said substrate; said at least two electrodes configured for transcutaneous stimulation of a pudendal nerve or surrounding perianal tissue or both; said substrate providing constant mechanical closure of the tissue surrounding the anal cavity is configured to operate synergistically with said transcutaneous stimulation of nerves or muscles to prevent expulsion of feces from said system; and wherein said adhesive portion is configured to enable absolute proximal interface between said at least two electrodes and skin surface of said user; said absolute proximal interface configured to provide increased transmission of electrical stimulation with lower resistance for a prolonged time period; said prolonged time period selected from the group consisting of at least one hour, at least two hours, at least four hours, at least six hours, at least eight hours, at least ten hours, at least twelve hours, at least sixteen hours, at least twenty hours and at least twenty-four hours.

2. The system according to claim 1, wherein said at least two electrodes are coupled using wired or wireless technologies to a control module that comprises a microprocessor for controlling operational parameters of said transcutaneous stimulation or electrical activity measurement.

3. The system according to claim 2, wherein said control module is coupled to at least one sensor in a control feedback loop.

4. The system according to claim 3, wherein said at least one sensor is configured to obtain measurements associated with muscle activity or neurological activity or both following said transcutaneous stimulation; said at least one sensor comprises at least one sensor selected from the group consisting of electromyography (EMG) sensors, impedance sensors, capacitance sensors, wetness sensors, pH sensors, temperature sensors, and position sensors.

5. The system according to claim 4, wherein said fecal blocking element is configured to provide tactile feedback by palpation; said fecal blocking element and said position sensors are configured to provide accurate positioning and placement of said system by said user over the anal opening; said accurate positioning of said system enables precise emplacement of said at least two electrodes in the vicinity of said fecal blocking element and pudendal nerve or surrounding perianal tissue or both.

6. The system according to claim 4, wherein said transcutaneous stimulation is based on learning of an effect and an occurrence of previous stimulation on said user; said learning is based on said obtained measurements and used to predict defecation and to activate electrical stimulation autonomically.

7. The system according to claim 4, wherein said obtained measurements are reported to a patient or physician and used to:

predict fecal incontinence frequency and patterns;

determine optimal electrical stimulation patterns;

adjust diet, prescription drugs and day-to-day behaviors; and regulate electrical stimulation properties or any other medical treatment.

8. The system according to claim 3, wherein said control module further comprises an on/off switch configured to activate targeted electrical stimulation when at least one of the following exist:

said user squeezes the buttocks together;

said EMG sensors sense a fecal urge sensation; and said impedance sensors, capacitance sensors, wetness sensors, pH sensors and temperature sensors sense leakage of feces;

wherein said targeted electrical stimulation comprises a stimulation pattern; said stimulation pattern comprises continuous or intermittent stimulation and is combined with voluntary contraction of anal sphincter muscles; said combination of targeted electrical stimulation and voluntary contraction of said anal sphincter muscles is configured to increase contraction forces until said fecal urge sensation is dismissed.

9. The system according to claim 2, wherein said control module is external to said substrate.

10. The system according to claim 1, wherein said adhesive portion comprises two adhesive layer types; said two adhesive layer types comprise a light skin adhesive layer for initial positioning and medium or strong skin adhesive layer for complete installment configured to:

enable absolute proximal interface between said substrate and skin surface during use;

prevent lateral movement of said substrate against a skin surface during use; and enable easy removal and disposal of said substrate after use.

11. The system according to claim 1, wherein intentional peeling of said adhesive portion during detachment and disposal of said system enables instantaneous removal of said at least two electrodes.

12. The system according to claim 1, wherein said rectal portion with said fecal blocking element is curved to fit in an anus of said user; said fecal blocking element is configured to achieve mechanical closure of said anal cavity and prevent expulsion of feces from said system.

13. The system according to claim 1, wherein said substrate is characterized by a shape selected from the group consisting of an elongate rectangular shape, an oval shape, a saddle shape, a G-string shape, and a garment shaped as underwear or panties.

14. The system according to claim 1, wherein said transcutaneous stimulation of a pudendal nerve or surrounding perianal tissue or both is used to verify said system is positioned as needed.

15. The system according to claim 1, wherein said transcutaneous stimulation of a pudendal nerve or surrounding perianal tissue or both is used to contract the muscles to reduce adhesiveness and allow easier removal of said system.

16. The system according to claim 1, wherein said transcutaneous stimulation of a pudendal nerve or surrounding perianal tissue or both is used to generate heat to reduce adhesiveness and allow easier removal of said system.

17. A method for treatment of fecal incontinence, said method comprising steps of:

affixing a system according to claim 1 externally against a skin surface of a user;

providing constant mechanical closure of the tissue surrounding the anal cavity with said multi-layer substrate and said transcutaneous stimulation of nerves or muscles to prevent expulsion of feces;

restricting feces from an episode of fecal incontinence with a blocking element with or without a high-absorbency fill component to prevent leakage of feces from said system;

retaining feces in said rectal portion with an impermeable cover layer until removal and disposal;

disposing retained feces in said rectal portion with or without a removable absorbent element;

replacing disposed rectal portion with or without an absorbent element with new rectal portion in said system.

* * * * *